United States Patent
Leflaive et al.

(10) Patent No.: US 10,112,182 B2
(45) Date of Patent: Oct. 30, 2018

(54) CATALYTIC ADSORBENT FOR THE CAPTURE OF ARSENIC AND THE SELECTIVE HYDRODESULFURIZATION OF GASOLINES

(71) Applicant: IFP ENERGIES NOUVELLES, Rueil-Malmaison (FR)

(72) Inventors: Philibert Leflaive, Mions (FR); Marie Claire Marion, Vernaison (FR); Antoine Daudin, Corbas (FR)

(73) Assignee: IFP ENERGIES NOUVELLES, Rueil-Malmaison (FR)

( * ) Notice: Subject to any disclaimer, the term of this patent is extended or adjusted under 35 U.S.C. 154(b) by 206 days.

(21) Appl. No.: 14/259,577

(22) Filed: Apr. 23, 2014

(65) Prior Publication Data

US 2014/0323778 A1 Oct. 30, 2014

(30) Foreign Application Priority Data

Apr. 26, 2013 (FR) .................................... 13 53828

(51) Int. Cl.
| | |
|---|---|
| *B01J 27/19* | (2006.01) |
| *C10G 45/32* | (2006.01) |
| *C10G 45/02* | (2006.01) |
| *C10G 25/00* | (2006.01) |
| *C07C 7/12* | (2006.01) |
| *B01J 23/882* | (2006.01) |

(52) U.S. Cl.
CPC ............. *B01J 27/19* (2013.01); *B01J 23/882* (2013.01); *C07C 7/12* (2013.01); *C10G 25/003* (2013.01); *C10G 45/02* (2013.01); *C10G 45/32* (2013.01); *C10G 2300/205* (2013.01)

(58) Field of Classification Search
CPC ................................ B01J 27/19; B01J 23/882
See application file for complete search history.

(56) References Cited

U.S. PATENT DOCUMENTS

| | | | |
|---|---|---|---|
| 4,111,795 A | | 9/1978 | Simpson |
| 5,401,392 A | * | 3/1995 | Courty ................. C10G 25/003 208/251 H |
| 7,981,828 B2 | | 7/2011 | Devers et al. |
| 2003/0111391 A1 | * | 6/2003 | Bhan ........................ B01J 23/85 208/253 |
| 2008/0053872 A1 | | 3/2008 | Devers et al. |

FOREIGN PATENT DOCUMENTS

EP    1892039 A1    2/2008

OTHER PUBLICATIONS

French Search Report dated Jan. 7, 2014 issued in corresponding FR 1353828 application (pp. 1-2).

* cited by examiner

*Primary Examiner* — Melvin C. Mayes
*Assistant Examiner* — Michael Forrest
(74) *Attorney, Agent, or Firm* — Millen White Zelano and Branigan, PC

(57) ABSTRACT

A catalytic adsorbent, comprising at least cobalt and molybdenum deposited on a porous substrate in which the content of cobalt, expressed in terms of CoO oxide, is between 11 and 30% by weight relative to the total weight of said adsorbent and the content of molybdenum, expressed in terms of $MoO_3$ oxide, is between 3 and 30% by weight relative to the total weight of said adsorbent, is described. This invention also relates to a process for hydrotreatment using said catalytic adsorbent.

21 Claims, No Drawings

CATALYTIC ADSORBENT FOR THE CAPTURE OF ARSENIC AND THE SELECTIVE HYDRODESULFURIZATION OF GASOLINES

FIELD OF THE INVENTION

This invention relates to the field of the hydrotreatment of gasoline fractions, in particular gasoline fractions obtained from fluidized-bed catalytic cracking units (FCC). More particularly, this invention relates to a catalytic adsorbent having the properties of capturing arsenic and simultaneously selectively desulfurizing a hydrocarbon-containing feedstock over time while preserving a high octane number. The invention also relates to a process for hydrotreatment using said catalytic adsorbent.

The specifications on automotive fuels call for a significant reduction in the sulfur contents in these fuels, and in particular in gasolines. This reduction is intended to limit, in particular, the contents of sulfur oxide and nitrogen oxide in automotive exhaust gases. European legislation refines the specifications for gasoline fuels. In 2009, they were at most 10 ppm by weight (parts per millions) of sulfur. To achieve these specifications, it is necessary to treat the gasolines by desulfurization processes. This content could again be revised to provide for further reduction in the coming years.

The primary sources of sulfur in the bases for gasolines are the so-called cracking gasolines and primarily the gasoline fraction that is obtained from a process for catalytic cracking of a residue of the atmospheric or vacuum distillation of a crude oil. The gasoline fraction obtained from catalytic cracking, which represents on average 40% of the gasoline bases, actually contributes more than 90% to the supply of sulfur in the gasolines. Consequently, the production of low-sulfur gasolines requires a stage of desulfurization of the catalytic cracking gasolines. Among the other gasoline sources that can contain sulfur are also cited coker gasolines, visbreaker gasolines, or, to a lesser extent, the gasolines that are obtained from atmospheric distillation or the steam-cracking gasolines.

The elimination of sulfur in the gasoline fractions consists in specifically treating these sulfur-rich gasolines by desulfurization processes in the presence of hydrogen. Reference is then made to hydrodesulfurization processes (HDS). However, these gasoline fractions and more particularly the gasolines that are obtained from FCC contain a major portion of unsaturated compounds in the form of monoolefins (approximately 20 to 50% by weight), which contribute to a good octane number, diolefins (0.5 to 5% by weight), and aromatic compounds. These unsaturated compounds are unstable and react during hydrodesulfurization treatment. The diolefins form gums by polymerization during hydrodesulfurization treatments. This formation of gums leads to a gradual deactivation of hydrodesulfurization catalysts or a gradual stoppering of the reactor. Consequently, the diolefins should be eliminated by hydrogenation before any treatment of these gasolines. The traditional treatment processes desulfurize the gasolines in a non-selective manner by hydrogenating a large portion of monoolefins, which results in a high loss in octane number and a heavy consumption of hydrogen. The most recent hydrodesulfurization processes make it possible to desulfurize the monoolefin-rich cracking gasolines, while limiting the hydrogenation of monoolefins and consequently the octane loss. Such processes are described in, for example, the documents EP-A-1077247 and EP-A-1174485.

The hydrodesulfurization processes are performed without interruption over periods of at least 3 to 5 years. The catalysts that are used for carrying out the hydrodesulfurization of sulfur-containing gasolines should therefore exhibit good activity, good selectivity, and good stability over time to be performed continuously for several years. However, the presence of heavy metals, such as mercury or arsenic, or contaminants such as phosphorus and silicon, in the form of organometallic compounds in the hydrocarbon-containing feedstocks that are to be desulfurized, brings about a quick deactivation of the hydrotreatment catalysts. It is therefore necessary to eliminate these contaminants from the feedstock before bringing them into contact with these hydrodesulfurization catalysts.

PRIOR ART

Different solutions are proposed to extract these impurities and more particularly arsenic in the hydrocarbon-containing feedstocks. In general, an adsorbent is placed either in a reactor located upstream from the hydrodesulfurization unit or in the hydrodesulfurization reactor, upstream from the catalytic bed that contains the hydrodesulfurization catalyst. Such adsorbents are described in the documents FR2794381 and WO2006/037884. These adsorbents are used in the presence of hydrogen, which has a drawback when the gasolines that are to be treated comprise unsaturated compounds. The result is a reduction in the octane number and a lowering of the quality of the gasoline under consideration starting from the stage of adsorption of impurities. These adsorbents also have the drawback of being not very active catalytically for the hydrodesulfurization reactions. Furthermore, they occupy a significant volume in the reactor, reducing the volume available for the hydrodesulfurization catalyst beds, and therefore bring about an overall loss of the performance of the process. It is therefore necessary to seek solutions that make it possible to eliminate these impurities, such as arsenic, with the objective of limiting the hydrogenation reactions that are responsible for a reduction in the octane number of the gasolines in question. These solutions should also make it possible to enhance the hydrodesulfurization performance and without loss of selectivity of the hydrodesulfurization reaction relative to the hydrogenation of olefins.

To this effect, the document EP-A-2072607 describes a process in a fixed bed for adsorption of arsenic and desulfurization of a hydrocarbon-containing feedstock by bringing it into contact with an adsorbent that has desulfurizing catalytic properties. This adsorbent makes it possible to capture arsenic and to desulfurize a hydrocarbon-containing feedstock while limiting the hydrogenation of monoolefins by combining both an element of group VIII and an element of group VIB. However, during its use over time, the hydrodesulfurization activity of this adsorbent is not adequate and greatly decreases. An increase of the reactions for hydrogenation of monoolefins is observed to the detriment of the hydrodesulfurization reactions. The catalytic activity of this adsorbent is very quickly reduced.

Thus, there is still a need for using an adsorbent solid of arsenic having properties for adsorption of heavy metals and catalytic properties for optimized hydrodesulfurization, i.e., presenting a good compromise between the hydrodesulfurization (HDS) activity and a maximum selectivity of hydrodesulfurization reactions relative to the reactions for hydrogenation of olefins (HDS/HYD) and whose properties for adsorption and catalytic activity after capture are stable over time. This invention proposes a new catalytic adsorbent for remedying the drawbacks of the adsorbents of the prior art.

SUMMARY AND ADVANTAGE OF THE INVENTION

This invention relates to a catalytic adsorbent, comprising at least cobalt and molybdenum deposited on a porous substrate in which the cobalt content, expressed in terms of CoO oxide, is between 11 and 30% by weight relative to the total weight of said adsorbent, and the content of molybdenum, expressed in terms of $MoO_3$ oxide, is between 3 and 30% by weight relative to the total weight of said adsorbent.

The applicant noted, surprisingly enough, that a catalytic adsorbent that comprised—as an active metal phase—cobalt and molybdenum, whose contents correspond to the conditions mentioned above, has not only a good capacity for adsorption of arsenic but also an activity in hydrodesulfurization and a selectivity in favor of hydrodesulfurization relative to the hydrogenation of olefins that are stable over time. Using the adsorbent according to the invention makes it possible to eliminate the arsenic and sulfur simultaneously from a hydrocarbon-containing feedstock also comprising monoolefins, over a long period of use, while selectively limiting the hydrogenation of monoolefins contained in said feedstock.

Another object of the invention is a process for hydrotreatment of a hydrocarbon-containing feedstock in which the hydrocarbon-containing feedstock is brought into contact in the presence of hydrogen with the catalytic adsorbent according to the invention, in particular, a process for adsorption of arsenic and for desulfurization of a hydrocarbon-containing feedstock comprising monoolefins, sulfur, and arsenic, in which said hydrocarbon-containing feedstock is brought into contact in the presence of hydrogen with the catalytic adsorbent according to the invention for producing an effluent whose sulfur content is reduced and low in arsenic and without an octane number loss.

"Catalytic adsorbent," also called "adsorbent" in the text below, is defined in terms of this invention as a solid that makes it possible to capture by adsorption impurities such as arsenic and that simultaneously makes it possible to eliminate the sulfur-containing compounds contained in the feedstock by a catalytic reaction in the presence of hydrogen.

DETAILED DESCRIPTION OF THE INVENTION

This invention relates to a catalytic adsorbent, comprising at least cobalt and molybdenum deposited on a porous substrate in which the content of cobalt, expressed in terms of CoO oxide, is between 11 and 30% by weight relative to the total weight of said adsorbent, and the content of molybdenum, expressed in terms of $MoO_3$ oxide, is between 3 and 30% by weight relative to the total weight of said adsorbent.

In a variant according to the invention, said catalytic adsorbent comprises a Co/Mo molar ratio of between 0.9 and 7, preferably between 1 and 6, and in a more preferred manner between 1 and 3.5.

In another preferred variant, said catalytic adsorbent has a cobalt content, expressed in terms of CoO oxide, of between 11 and 25% by weight, preferably between 15 and 25% by weight relative to the total weight of said adsorbent.

According to an advantageous embodiment, the catalytic adsorbent comprises a content of molybdenum, expressed in terms of $MoO_3$ oxide, of between 5 and 20% by weight and in a more preferred manner between 5 and 16% by weight relative to the total weight of said adsorbent.

The catalytic adsorbent according to the invention advantageously also comprises phosphorus. In this case, the phosphorus content, expressed in terms of $P_2O_5$ oxide, is between 0.2 and 8% by weight relative to the total weight of said adsorbent, in a preferred manner between 0.3 and 5% by weight, and in a more preferred manner between 0.4 and 4% by weight.

The metals of said catalytic adsorbent are deposited on an amorphous mineral substrate that is selected from the group that consists of aluminas, silica, silica-aluminas, silicon carbide, titanium oxides by themselves or in a mixture with alumina, or silica-alumina, the magnesium oxides by themselves or in a mixture with alumina, or silica-alumina. Preferably, the substrate is selected from the group that consists of aluminas, silica, and silica-aluminas. In a very preferred manner, the substrate essentially consists of at least one alumina, i.e., it comprises at least 51% by weight, preferably at least 60% by weight, in a very preferred manner at least 80% by weight, and even at least 90% by weight. The alumina can have different crystalline shapes, such as, for example, alpha-alumina, beta-alumina, gamma-alumina, delta-alumina, eta-alumina, theta-alumina, boehmite, or mixtures thereof. The specific surface area of the catalyst is between 50 and 350 $m^2/g$, preferably between 70 and 300 $m^2/g$, and in a very preferred manner between 90 and 250 $m^2/g$. The specific surface area is measured by the BET technique (standard ASTM D3663) on the solid in the oxide state. The porosity is such that the latter has a pore volume of between 0.4 and 1.4 $cm^3/g$, preferably between 0.5 and 1.3 $cm^3/g$. The pore volume is measured by mercury porosimetry according to the standard ASTM D4284-92 with a wetting angle of 140°.

The metals are deposited on the substrate of the catalytic adsorbent according to the invention according to techniques that are well known to one skilled in the art, for example by impregnation starting from a metal precursor solution. The impregnation can be done, for example, according to the known dry impregnation mode, in which the desired quantity of elements is introduced in the form of salts that are soluble in the selected solvent, for example demineralized water, in such a way as to fill up as precisely as possible the porosity of the substrate. The substrate that is thus filled by the solution is preferably dried. The preferred substrate is the alumina that can be prepared starting from any type of precursor and tools for shaping that are known to one skilled in the art.

The metals can be deposited by co-impregnation or by successive addition.

According to a first embodiment, metal cobalt and metal molybdenum are deposited on the substrate in a single stage, by dry impregnation of said substrate by means of a solution containing the desired quantity of cobalt and molybdenum.

Alternatively, according to a second embodiment, the cobalt is deposited by impregnation in a first stage, and next the molybdenum, or conversely the molybdenum and next the cobalt. According to a third embodiment, a first impregnation stage is carried out on the substrate of metal cobalt and metal molybdenum. A second impregnation of cobalt or molybdenum by itself is next carried out, so as to adjust the Co/Mo molar ratio. In this second or third embodiment, before the second impregnation, the impregnated substrate is dried and optionally calcined.

If the catalyst comprises phosphorus, the latter can be added into the impregnation solutions or optionally be deposited after deposition of cobalt and molybdenum.

Advantageously, as a solution for impregnation of cobalt, a solution that contains cobalt nitrate, cobalt hydroxide, or cobalt carbonate is used, by itself or in a mixture. As a solution for impregnation of molybdenum, a solution containing ammonium heptamolybdate or molybdenum oxide, by itself or in a mixture, is advantageously used. When the phosphorus is present in the catalytic adsorbent according to the invention, the phosphoric acid in an impregnation solution is advantageously used as a precursor. However, any other salt that is known to one skilled in the art having an adequate solubility in aqueous and decomposable solution during a drying stage or any type of oxidizing treatment can also be used.

After metals and optionally phosphorus are introduced, the catalytic adsorbent according to the invention is preferably subjected to a calcination treatment. This treatment has as its object to transform the molecular precursors of metals into the oxide phase. In this case, it is a matter of an oxidizing treatment, but a simple drying of the catalytic adsorbent can also be carried out. In a preferred manner, the catalytic adsorbent is subjected to a calcination treatment, prior to its use in the hydrodesulfurization process according to the invention. Said calcination treatment is advantageously used in air or in dilute oxygen, at a temperature of between 200° C. and 550° C., preferably between 300° C. and 500° C.

After calcination, the metals that are deposited on the substrate are in oxide form. Advantageously, the calcined catalytic adsorbent is also subjected to a sulfurization treatment before its use in the hydrodesulfurization process according to the invention. Sulfurization is done in a sulforeducing medium, i.e., in the presence of $H_2S$ and hydrogen, so as to transform the metal oxides into sulfides of transition metals, such as $MoS_2$, $Ni_3S_2$, and $Co_9S_8$. The sulfurization is carried out by injecting in the catalytic adsorbent a stream containing $H_2S$ and hydrogen, or else a sulfur-containing compound that can decompose into $H_2S$ in the presence of the catalytic adsorbent and hydrogen. The polysulfides such as dimethyl disulfide are $H_2S$ precursors that are commonly used for sulfurizing catalysts. The temperature is adjusted so that $H_2S$ reacts with metal oxides to form metal sulfides. This sulfurization can be done in situ or ex situ (inside or outside the hydrodesulfurization reactor) at temperatures of between 200 and 600° C., and more preferably between 300 and 500° C. To be active, the metals should be substantially sulfurized. An element is considered to be substantially sulfurized when the molar ratio between the sulfur (S) that is present in the catalytic adsorbent and said element is at least equal to 60% of the theoretical molar ratio corresponding to the total sulfurization of the element being considered:

$$(S/\text{element})_{catalytic\ adsorbent} \geq 0.6 \times (S/\text{element})_{theoretical}$$

with:

(S/element)$_{catalytic\ adsorbent}$ molar ratio between the sulfur (S) and the element that is present in the catalytic adsorbent.

(S/element)$_{theoretical}$ molar ratio between the sulfur and the element corresponding to the total sulfurization of the sulfide element.

This theoretical molar ratio varies according to the element being considered:

(S/Co)$_{theoretical}$=8/9

(S/Mo)$_{theoretical}$=2/1

The molar ratio between the sulfur that is present in the adsorbent and all of the elements is preferably at least equal to 60% of the theoretical molar ratio corresponding to the total sulfurization of each sulfide element, with the calculation being done in proportion to the relative molar fractions of each element.

After sulfurization, the catalytic adsorbent according to the invention is ready to be used in a process for adsorption of arsenic and hydrodesulfurization of a hydrocarbon-containing feedstock comprising unsaturated compounds.

Another object of the invention is a process for hydrotreatment of a hydrocarbon-containing feedstock in which the hydrocarbon-containing feedstock is brought into contact, in the presence of hydrogen, with the catalytic adsorbent according to the invention. Within the framework of this invention, the hydrotreatment process according to the invention is a process for adsorption of arsenic and optionally silicon and at least partial desulfurization of the hydrocarbon-containing feedstock in the presence of hydrogen for producing an effluent with a reduced sulfur content and low in heavy metals, in particular arsenic, with a limited loss of the octane number.

The hydrotreatment process according to the invention makes it possible to eliminate the arsenic and to transform simultaneously a portion of the organic sulfur-containing compounds into $H_2S$. It also makes it possible to limit the hydrogenation rate of the monoolefins and diolefins. The hydrogenation rate of the olefins is advantageously less than 50%, preferably less than 30%, and in an even more preferred manner less than 20%.

The hydrocarbon-containing feedstock that is to be treated is a catalytic cracking gasoline obtained from units for catalytic cracking, thermal cracking, or steam-cracking. The process can also apply to the treatment of mixtures of direct distillation gasolines that can contain heavy metals obtained from crude with cracking gasolines comprising monoolefins and diolefins. In a preferred manner, the hydrocarbon-containing feedstock that is to be treated is a catalytic cracking gasoline comprising between 5% and 60% by weight of monoolefins, between 50 ppm and 6,000 ppm by weight of sulfur-containing compounds, and between 10 and 1,000 ppb by weight of arsenic.

The sulfur-containing compounds contained in the hydrocarbon-containing feedstock that is to be treated can be organic sulfur-containing compounds, such as, for example, mercaptans, thiophenic compounds, benzothiophenic compounds, and other aromatic sulfur-containing compounds, disulfite compounds, etc.

The arsenical compounds contained in the hydrocarbon-containing feedstock that is to be treated can be organic arsenical compounds, such as, for example, trimethylarsine or triethylarsine. The monoolefins refer to hydrocarbon-containing molecules having a unique double carbon-carbon bond, and the diolefins are hydrocarbon-containing molecules comprising at least two double carbon-carbon bonds. The monoolefins and the diolefins can be linear, branched and/or cyclic hydrocarbon-containing molecules.

The catalytic adsorbent according to the invention is advantageously used under operating conditions such that the adsorption rate of the arsenic is maximized, while limiting the hydrogenation rate of the olefins.

The contact is made generally at a temperature of between 200 and 400° C., at a pressure of between 0.2 and 5 MPa, and with a ratio of the hydrogen flow rate to the hydrocarbon-containing feedstock flow rate of between 50 and 800 $Nm^3/m^3$.

Advantageously, the catalytic adsorbent is subjected to a calcination treatment prior to its use. Preferably, according to the invention, the calcined catalytic adsorbent is also subjected to a sulfurization treatment before its use. Advantageously, said sulfurization is carried out in such a way that the sulfurization rate of the metals constituting said catalytic adsorbent is at least 60%.

The hydrogen that is used can be obtained from any hydrogen source. Preferably, fresh hydrogen that is obtained from the refinery and/or recycled hydrogen from a hydrodesulfurization unit, preferably from the hydrodesulfurization unit of the hydrocarbon-containing fraction that is to be purified, is used.

Several reactor technologies can be considered for carrying out adsorption and hydrodesulfurization of a hydrocarbon-containing feedstock in the presence of catalytic adsorbent according to the invention, with the most standard and most widely used technology being the fixed-bed technology. In this case, a reactor is charged with catalytic adsorbent according to the invention, operating by adsorption of arsenic and by hydrodesulfurization, basically until arsenic appears in the output effluent (a phenomenon that is known to one skilled in the art by the term piercing). In some cases, the total quantity of poisoned adsorbent can be replaced by an equivalent quantity of fresh adsorbent. The selection of a replacement technology for catalytic adsorbent according to the invention is not considered within the framework of this invention to be a limiting factor. The catalytic adsorbent can be used in a moving-bed reactor; i.e., the spent adsorbent is drawn off continuously and replaced by fresh catalytic adsorbent. This type of technology makes it possible to maintain the capture of arsenic by catalytic adsorbent and to prevent the piercing of the latter in the effluents that are produced. Among other solutions are also cited the use of expanded-bed reactors that also makes possible a continuous drawing-off and addition of catalytic adsorbent so as to maintain the hydrodesulfurization activity of the catalytic adsorbent.

The hydrotreatment process according to the invention is preferably coupled with at least one catalytic hydrodesulfurization stage or complementary selective hydrogenation stage that is carried out on the effluent that is obtained from contact with the catalytic adsorbent according to the invention. Thus, the stage of treatment of the hydrocarbon feedstock by the adsorbent is regarded as a pretreatment that makes it possible in particular to preserve the catalytic activity of the catalyst that is used in the hydrodesulfurization stage or subsequent selective hydrogenation stage.

Thus, the hydrotreatment process according to the invention comprises one or more other complementary stages for hydrodesulfurization or selective hydrogenation in which the effluent that is obtained from bringing the hydrocarbon-containing feedstock into contact with the catalytic adsorbent according to the invention is brought into contact with at least one other catalyst for hydrodesulfurization or selective hydrogenation of diolefins that are present in the olefin feedstock. Said complementary hydrodesulfurization stage(s) make(s) it possible to eliminate the residual sulfur-containing compounds contained in the effluent that is low in arsenic and with a lower sulfur content. Some of these residual sulfur-containing compounds can be obtained from the addition of $H_2S$ to the olefins that are present in the feedstock. $H_2S$ can form when the hydrocarbon feedstock is brought into contact with the catalytic adsorbent, i.e., during the adsorption of arsenic and the desulfurization using the catalytic adsorbent according to the invention.

Said complementary hydrodesulfurization stage(s) is (are) used when the effluent that is obtained from bringing the hydrocarbon-containing feedstock into contact with the catalytic adsorbent generally has a sulfur content that is higher than 10 ppm and that is necessary to produce gasolines with a low sulfur content corresponding to the current specifications that are less than 10 ppm in many countries. The effluent from which arsenic and a portion of the sulfur-containing compounds are removed is then treated in at least one of said complementary stages of selective hydrodesulfurization. In said stage(s), said effluent is brought into contact with at least one other catalyst for hydrodesulfurization under operating conditions that may be identical or different from those for bringing the hydrocarbon-containing feedstock into contact with the catalytic adsorbent.

Said catalyst(s) used in said complementary hydrodesulfurization stage(s) is (are) protected from deactivation by the arsenic that is present in the feedstock by means of the catalytic adsorbent according to the invention. Thus, very selective hydrodesulfurization catalysts that are sensitive to the presence of arsenic can be used in said complementary hydrodesulfurization stage(s). Any hydrodesulfurization catalyst can be used in said complementary hydrodesulfurization stage(s).

Preferably, catalysts that have a high selectivity relative to hydrodesulfurization reactions relative to the hydrogenation reactions of olefins are used. Such catalysts comprise at least one amorphous and porous mineral substrate, a metal of group VIB, and a metal of group VIII. The metal of group VIB is preferably molybdenum or tungsten, and the metal of group VIII is preferably nickel or cobalt. The substrate is generally selected from the group that consists of aluminas, silica, silica-aluminas, silicon carbide, titanium oxides by themselves or in a mixture with alumina or silica-alumina, the magnesium oxides by themselves or in a mixture with alumina, or silica-alumina. Preferably, the substrate is selected from the group that consists of aluminas, silica, and silica-aluminas. Preferably, the hydrodesulfurization catalyst that is used in the complementary hydrodesulfurization stage or stages has the following characteristics:

The content of elements of group VIB is between (inclusive) 1 and 20% by weight of oxides of elements of group VIB;

The content of elements of group VIII is between (inclusive) 0.1 and 20% by weight of oxides of elements of group VIII;

The molar ratio (elements of group VIII/elements of group VIB) is between (inclusive) 0.1 and 0.8.

A very preferred hydrodesulfurization catalyst comprises cobalt and molybdenum and has the characteristics mentioned above.

Furthermore, the hydrodesulfurization catalyst can comprise phosphorus. In this case, the phosphorus content is preferably between (inclusive) 0.1 and 10% by weight of $P_2O_5$ relative to the total catalyst weight, and the molar ratio of phosphorus to the elements of group VIB is greater than or equal to 0.25, preferably greater than or equal to 0.27.

In said complementary hydrodesulfurization stage(s), the effluent with the lower sulfur content and that is low in arsenic obtained from bringing the hydrocarbon-containing feedstock into contact with the catalytic adsorbent according to the invention is brought into contact with at least one other catalyst for selective hydrodesulfurization under the following operating conditions:

A temperature of between approximately 210 and approximately 410° C., preferably between 240 and 360° C.;

A total pressure of between 0.2 and 5 MPa, and more preferably between 0.5 and approximately 3 MPa;

A ratio of volume of hydrogen per volume of hydrocarbon-containing feedstock of between 50 and 800 $Nm^3/m^3$, and more preferably between 60 and 600 $Nm^3/m^3$.

In a variant of the process according to the invention, the operating conditions for bringing the hydrocarbon-containing feedstock into contact with the catalytic adsorbent according to the invention are identical to those used in said complementary hydrodesulfurization stage(s).

According to another embodiment, the stage of hydrotreatment of the effluent that is obtained from the adsorption stage by means of the adsorption mass according to the invention is a selective hydrogenation that makes possible the hydrogenation of diolefins into olefins and optionally unsaturated sulfur-containing compounds, but also the transformation (increasing the weight) of the light sulfur-containing compounds (i.e., having a temperature that is lower than that of thiophene) into sulfur-containing compounds whose temperature is higher than that of thiophene, for example by addition of mercaptans to olefins.

This hydrogenation stage is carried out in the presence of hydrogen and a catalyst containing at least one metal of group VIb and at least one non-noble metal of group VIII deposited on a porous substrate. Preferably, a catalyst is used of which:

The content by weight of oxide of the element of group VIb is between 6 and 18% relative to the weight of the catalyst;

The content by weight of oxide of the element of group VIII is between 4 and 12% relative to the weight of the catalyst;

The specific surface area of the catalyst is between 200 and 270 $m^2/g$;

The density of the element of group VIb, expressed as being the ratio between said content by weight of oxide of the element of group VIb and the specific surface area of the catalyst is between 4 and $6 \cdot 10^{-4}$ $g/m^2$;

The molar ratio between the metal of group VIII and the metal of group VIb is between 0.6 and 3 mol/mol.

The metal of group VIb is preferably selected from among molybdenum and tungsten; in a very preferred manner, the metal of group VIb is molybdenum.

The metal of group VIII is preferably nickel and/or cobalt, in a very preferred manner nickel.

Hydrogen is generally introduced that slightly exceeds, up to 5 mol per mol, the stoichiometry that is necessary for hydrogenating the diolefins (one mol of hydrogen per mol of diolefin). The mixture that consists of gasoline and hydrogen is brought into contact with the catalyst under a pressure of between 0.5 and 5 MPa, a temperature of between 80 and 220° C., with a liquid volumetric flow rate (LHSV) of between 1 and 10 $h^{-1}$, with the liquid volumetric flow rate being expressed in terms of liter of feedstock per liter of catalyst and per hour (L/L·h).

In a variant of the process according to the invention, the catalytic adsorbent according to the invention can be placed in a guard-bed position of one or more reactor(s) containing the catalyst(s) used in said complementary stage(s) of hydrodesulfurization and/or selective hydrogenation.

In another variant of the process according to the invention, the catalytic adsorbent according to the invention is placed in a so-called adsorption reactor. This reactor is separated and is placed upstream from the reactor(s) containing the catalyst(s) used in said complementary stage(s) for hydrodesulfurization and/or selective hydrogenation.

In all of the variants of the process according to the invention, using at least one complementary stage of hydrodesulfurization and/or selective hydrogenation, the ratio of the volume of the catalytic adsorbent according to the invention relative to the volume of the catalyst(s) used in said complementary stage(s) of hydrodesulfurization and/or selective hydrogenation is advantageously between 4 and 50%, preferably between 5 and 40%, and in a more preferred manner between 5 and 35%.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing and in the examples, all temperatures are set forth uncorrected in degrees Celsius and, all parts and percentages are by weight, unless otherwise indicated.

The entire disclosures of all applications, patents and publications, cited herein and of corresponding application No. FR 13/53.828, filed Apr. 26, 2013 are incorporated by reference herein.

EXAMPLES

The following examples illustrate the invention without thereby limiting the scope thereof.

Example 1: Preparation of Adsorbent Solids

Three adsorbents are prepared by dry impregnation of an alumina substrate from an aqueous solution containing the precursors of cobalt and molybdenum. The latter are cobalt nitrate and ammonium heptamolybdate for the solids A and B. In the case of the solid C, the precursors are cobalt hydroxide, molybdenum oxide, and phosphoric acid. At the end of the impregnation stage, the solids are allowed to mature for 2 hours and then vacuum-dried in a furnace at 90° C. for one night, and then calcined at 450° C. for 6 hours.

At the end of their preparation, the contents of Co, Mo, and P are determined by X-ray fluorescence. The results, expressed in terms of % by weight of CoO, $MoO_3$, and $P_2O_5$ oxides are provided in Table 1 below:

TABLE 1

Characteristics of Solids

| Solid | A (For Comparison) | B (According to the Invention) | C (According to the Invention) |
|---|---|---|---|
| CoO (% by Weight) | 2.3 | 20 | 20 |
| $MoO_3$ (% by Weight) | 8 | 8 | 10 |
| $P_2O_5$ (% by Weight) | — | — | 1.4 |
| Co/Mo (Atomic Ratio) | 0.3 | 2.9 | 2.4 |

Example 2: Evaluation of the Catalytic Performance and Capture of Arsenic

Next, the evaluation of these solids for their performance of hydrodesulfurization of a gasoline that is obtained from FCC (fraction 50-245° C.) containing 360 ppm by weight of sulfur is initiated. So as to evaluate the performance of solids for the capture of arsenic, a portion of this feedstock is doped by an arsenical compound (triphenylarsine) in such a way as to reach a concentration of 3,000 ppb by weight of arsenic.

To carry out these tests, a pilot unit that is equipped with a tubular reactor with a flow-through fixed bed is used.

The quantity of arsenic in the feedstock and in the effluents is measured by atomic absorption, the sulfur in the feedstock and in the effluents is determined by X-ray fluorescence, and the olefins in the feedstock and in the effluents are analyzed by gas phase chromatography. These values thus make it possible to calculate the yields of hydrodesulfurization (HDS), hydrogenation of olefins (HydO), and capture of arsenic (HDAs).

The adsorbent solids are evaluated under the same conditions, presented in detail below.

To conduct the reactions, 20 ml of adsorbent solids is introduced into the reactor and is sulfurized at 350° C. under a gaseous mixture ($H_2/H_2S$) at (85/15) % vol./vol.

In a first phase, the FCC gasoline is first injected in the presence of $H_2$ ($H_2$/feedstock ratio=300 Nl/l), and the performance of HDS, HydO, and HDAs is followed over time at 250° C. and under a total pressure of 2 MPa. This first phase is conducted with an FCC gasoline without arsenic with a VVH of 4 $h^{-1}$ for determining the initial HDS and HydO performance of the adsorbent solids. The duration of this first phase is fixed at 150 hours.

Next, the second phase, which consists in treating the FCC gasoline into which arsenic (added compound=triphenylarsine) was introduced, is begun. The temperature and pressure conditions are identical to the first phase with the exception of the VVH that is increased to 10 $h^{-1}$.

The results that are obtained for the three solids A, B, and C are presented in Table 2 below. The indicated piercing time corresponds to the time at the end of which the arsenic content in the effluent is greater than or equal to 1% of the arsenic content in the feedstock ($C/C_o \geq 1\%$ m/m).

TABLE 2

Catalytic Performance of Solids

| | Solid A (For Comparison) | Solid B (According to the Invention) | Solid C (According to the Invention) |
|---|---|---|---|
| HDS and HydO Yields After 150 Hours at VVH 10 $h^{-1}$: | | | |
| HDS (% by Weight) | 28.6 | 27.0 | 26.5 |
| HydO (% by Weight) | 2.0 | 2.2 | 1.8 |
| HDAs Yield: | | | |
| Piercing Time (h) | 24 | 680 | 690 |
| Yields After 700 Hours and at VVH 10 $h^{-1}$ | | | |
| HDAs (% by Weight) | 88.2 | 99.7 | 99.6 |
| HDS (% by Weight) | 10 | 22 | 21 |
| HydO (% by Weight) | 2.4 | 2.2 | 2.1 |

It is observed that the solids A (not in accordance with the invention) and the solids B, C (in accordance with the invention) have a comparable performance in terms of hydrodesulfurization and hydrogenation of olefins before the injection of arsenic into the gasoline that is to be treated.

Moreover, the adsorbent solids B and C according to the invention have a better capacity for adsorption of arsenic than the solid A; this is reflected by a period before piercing that is multiplied by approximately 28 for the adsorbent solids B and C relative to the solid A.

It is also noted that the adsorbent solids B and C also preserve a good HDS activity relative to the adsorbent solid A after 700 hours of use. Thus, a drop in HDS yields of 18.5% and 20.8% is observed for the adsorbent solids B and C respectively while for the solid A, this drop is 65% after 700 hours.

Finally, it is remarked that the adsorbent solids B and C, after 700 hours, also have a low hydrogenation activity of olefins.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A catalytic adsorbent comprising at least cobalt and molybdenum deposited on a porous substrate in which the content of cobalt, expressed in terms of CoO oxide, is between 20 and 25% by weight relative to the total weight of said adsorbent, and the content of molybdenum, expressed in terms of $MoO_3$ oxide, is between 3 and 30% by weight relative to the total weight of said adsorbent and in which the Co/Mo molar ratio is between 1 and 6, and wherein the cobalt and molybdenum are in part in sulfur form, the content and ratios of Co and Mo being determined before adding sulfur to put them part in sulfur form.

2. The adsorbent according to claim 1, in which the Co/Mo molar ratio is between 1 and 3.5.

3. The adsorbent according to claim 1, in which the molybdenum content, expressed in terms of $MoO_3$ oxide, is between 5 and 20% by weight relative to the total weight of said adsorbent.

4. The adsorbent according to claim 1, additionally comprising phosphorus.

5. The adsorbent according to claim 4, in which the phosphorus content, expressed in terms of $P_2O_5$ oxide, is between 0.2 and 8% by weight relative to the total weight of said adsorbent.

6. The adsorbent according to claim 1, in which the cobalt content, expressed in terms of CoO oxide, is between 21 and 25% by weight relative to the total weight of said adsorbent.

7. The adsorbent according to claim 1, in which the molybdenum content, expressed in terms of $MoO_3$ oxide, is between 21 and 30% by weight relative to the total weight of said adsorbent.

8. The adsorbent according to claim 1, in which the Co/Mo molar ratio is between 3.5 and 6.

9. The adsorbent according to claim 1, in which the Co/Mo molar ratio is between 2 and 3.

10. The adsorbent according to claim 1, in which the molybdenum content, expressed in terms of $MoO_3$ oxide, is between 16 and 20% by weight relative to the total weight of said adsorbent.

11. A catalytic adsorbent comprising at least cobalt and molybdenum deposited on a porous substrate in which the content of cobalt, expressed in terms of CoO oxide, is 20% by weight relative to the total weight of said adsorbent, and the content of molybdenum, expressed in terms of $MoO_3$ oxide, is between 8 and 10% by weight relative to the total weight of said adsorbent and in which the Co/Mo molar ratio is between 2.4 and 2.9, and wherein the cobalt and molybdenum are in part in sulfur form.

12. The adsorbent according to claim 1, in which the molar ratio between the sulfur (S) that is present in the catalytic adsorbent and the cobalt and molybdenum is at least equal to 60% of the theoretical molar ratio corresponding to the total sulfurization of said cobalt and molybdenum.

13. A process for hydrotreatment of a hydrocarbon-containing feedstock comprising at least one catalytic adsorption stage in which the hydrocarbon-containing feedstock is brought into contact, in the presence of hydrogen, with the catalytic adsorbent according to claim 1.

14. The process according to claim 13, in which the catalytic adsorbent is subjected to a calcination treatment prior to its use.

15. The process according to claim 14, in which the calcined catalytic adsorbent is also subjected to a sulfurization treatment before its use.

16. The process according to claim 15, in which the sulfurization is carried out in such a way that the sulfurization rate of the metals constituting said catalytic adsorbent is at least 60%.

17. The process according to claim 13, in which the contact is made at an operating temperature of between 200 and 400° C., an operating pressure of between 0.2 and 5 MPa, and a ratio of the hydrogen flow rate to the flow rate of the hydrocarbon-containing feedstock of between 50 and 800 $Nm^3/m^3$.

18. The process according to claim 13, in which the effluent that is obtained from being brought into contact with the adsorbent is brought into contact with at least one catalyst for hydrodesulfurization or selective hydrogenation.

19. The process according to claim 18, in which the contact with the catalyst for hydrodesulfurization or the catalyst for selective hydrogenation is made in the same reactor that contains adsorbent.

20. The process according to claim 18, in which the ratio of the volume of said catalytic absorbent relative to the volume of said catalyst for hydrodesulfurization or selective hydrogenation is between 4 and 50%.

21. The process according to claim 13, in which the hydrocarbon-containing feedstock is a catalytic cracking gasoline containing between 5 and 60% by weight of monoolefins, between 50 and 6,000 ppm by weight of sulfur-containing compounds, and between 10 and 1,000 ppb by weight of arsenic.

* * * * *